United States Patent [19]

Lafon

[11] Patent Number: 4,489,095
[45] Date of Patent: Dec. 18, 1984

[54] HALOGENOBENZHYDRYLSUL-FINYLACETOHYDROXAMIC ACIDS

[75] Inventor: Louis Lafon, Paris, France
[73] Assignee: Laboratoire L. Lafon, France
[21] Appl. No.: 498,592
[22] Filed: May 26, 1983

[30] Foreign Application Priority Data

Jun. 4, 1982 [FR] France .................. 82 09805

[51] Int. Cl.³ .............. C07C 83/10; A61K 31/185
[52] U.S. Cl. ................... 424/315; 260/500.5 H
[58] Field of Search ............ 260/500.5 H; 424/315

[56] References Cited

U.S. PATENT DOCUMENTS

| | | |
|---|---|---|
| 2,483,671 | 10/1949 | Rieveschl . |
| 2,618,637 | 11/1952 | Archer et al. . |
| 3,157,650 | 11/1964 | Habicht . |
| 3,549,691 | 12/1970 | Leigh et al. . |
| 3,789,072 | 1/1974 | Bernstein . |
| 3,993,683 | 11/1976 | Nickl et al. . |
| 4,013,776 | 3/1977 | Lafon .................. 260/500.5 H |
| 4,062,973 | 12/1977 | Nickl et al. . |
| 4,066,686 | 1/1978 | Lafon .................. 260/500.5 H |
| 4,122,186 | 10/1978 | Lafon .................. 260/500.5 H |
| 4,134,996 | 1/1979 | Dunbar et al. . |
| 4,156,011 | 5/1979 | Lafon et al. . |
| 4,177,290 | 12/1979 | Lafon . |
| 4,183,927 | 1/1980 | Begin et al. . |
| 4,199,597 | 4/1980 | Neustadt et al. . |

FOREIGN PATENT DOCUMENTS 61406 9/1982 European Pat. Off. ...... 260/500.5 H
2326181 4/1977 France .
2385693 10/1978 France .

OTHER PUBLICATIONS

Buraczewski, et al., Bull. Acad. Polon. Sci. Ser. Sci. Chim. vol. XII No. 11, 1964.
J. Org. Chem., vol. 32, Oct. 1967, pp. 3191-3194.

Primary Examiner—J. E. Evans
Attorney, Agent, or Firm—Brumbaugh, Graves, Donohue & Raymond

[57] ABSTRACT

The present invention relates to new industrial products, namely halogeno-benzhydrylsulfinylacetohydroxamic acids of formula:

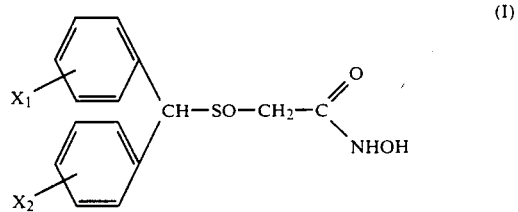

wherein:
$X_1$ is F, Cl, Br or $CF_3$; and
$X_2$, which may be identical to or different from $X_1$, is H, F, Cl, Br or $CF_3$.

These products are useful in therapeutics, particularly as substances acting on the CNS.

2 Claims, No Drawings

HALOGENOBENZHYDRYLSULFINYLACETOHYDROXAMIC ACIDS

The present invention relates to new compounds belonging to the family of benzhydrylsulfinylacetohydroxamic acids and having at least one halogen group such as F, Cl, Br or $CF_3$ on one of the phenyl groups of the benzhydryl radical. The invention also relates to a method for preparing these new compounds and to the use thereof in therapeutics, particularly as substances active on the central nervous system (CNS).

U.S. Pat. No. 4,066,686 discloses a certain number of benzhydrylsulfinyl-hydroxamic acids of formula

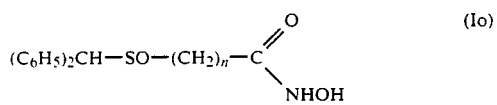

(wherein n is 1, 2 or 3). The compounds of formula (Io) are also known to be substances which act on the CNS. In particular, it is known that benzhydrylsulfinylacetohydroxamic acid (cf. Example 1 of the above-mentioned patent; Code No.: CRL 40028) is an excellent psychotonic agent and that benzhydrylsufinylpropionhydroxamic acid (cf. Example 6 of said patent; Code No.: CRL 40206) and benzhydrylsulfinylbutyrohydroxamic acid (cf. Example 9 of said patent; Code No.: CRL 40278) are sedative substances.

Unexpectedly, it has been found that the halogeno compounds of formula I, infra, are substances (i) useful as psychotonic agents, and (ii) endowed with anti-aggressive properties. The psychotonic compound of the 3686 patent, i.e., benzhydrylsulfinylacetohydroxamic acid, does not exhibit any anti-aggressive properties.

The new derivatives of benzhydrylsulfinylacetohydroxamic acid according to the invention are characterized in that they are selected from the group consisting of the halogeno-benzhydrylsulfinylacetohydroxamic acids of general formula

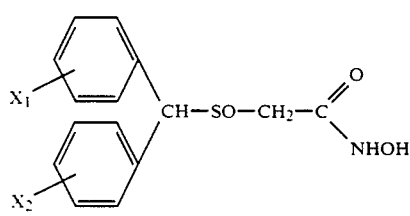

wherein
$X_1$ is F, Cl, Br or $CF_3$; and
$X_2$, which may be identical to or different from $X_1$, is H, F, Cl, Br or $CF_3$.

The preferred compounds according to the invention are those which have in their structural formula the groups $X_1$ and $X_2$ in para position. Among such compounds, particular mention may be made of the 4-chloro, 4-fluoro, 4,4'-dichloro and 4,4'-difluoro derivatives. The most interesting compound from the therapeutical point of view is 4,4-difluoro-benzhydrylsulfinylacetohydroxamic acid.

By way of illustration, Table I, infra, shows some examples of compounds according to the invention (Example 1-Example 8) and prior known homologues of the above-mentioned U.S. patent (A1-A3).

From the neuropsychopharmacological standpoint, the halogeno derivatives according to the invention are psychotonic agents. Like CRL 40028 (compound A1), they increase the spontaneous motility in the mouse and improve motorial recovery in the mouse in which the motility had been reduced both by habituation to its enclosure and by hypoxic aggression. On the other hand, CRL 40260 (compound A2) and CRL 40278 (compound A3) reduce the spontaneous motility in the mouse and do not bring about any recovery of the motorial activity in the mouse in which the motility had been reduced. The principle difference between the halogeno derivatives according to the invention and the psychotonic compound (A1) resides in the fact that said novel halogeno derivatives have anti-aggressive properties, whilst the known compound (A1) does not exhibit such properties.

TABLE I

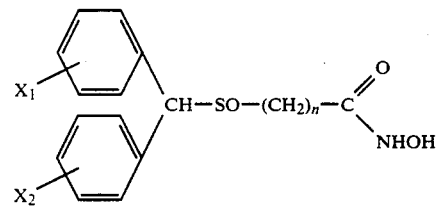

| Compound | Code No. | $X_1$ | $X_2$ | n | Effect on the CNS |
|---|---|---|---|---|---|
| Example 1 | CRL 40941 | 4-F | 4-F | 1 | (b) |
| Example 2 | CRL 40933A | 4-Cl | H | 1 | (b) |
| Example 3 | CRL 41018A | 4-F | H | 1 | (b) |
| Example 4 | CRL 40933B | 4-Cl | 4-Cl | 1 | (b) |
| Example 5 | — | 4-Br | 4-Br | 1 | (b) |
| Example 6 | — | $4-CF_3$ | H | 1 | (b) |
| Example 7 | — | $4-CF_3$ | $4-CF_3$ | 1 | (b) |
| Example 8 | — | 4-Br | H | 1 | (b) |
| A1 (a) | CRL 40028 | H | H | 1 | (b) |
| A2 (a) | CRL 40260 | H | H | 2 | (c) |
| A3 (a) | CRL 40278 | H | H | 3 | (c) |

Notes:
(a) described in U.S. Pat. No. 4 066 686;
(b) psychotonic
(c) sedative

The comparative tests undertaken to assess the anti-aggressive properties mentioned above have been summarized hereinbelow.

The modus operandi is as follows: After having spent 3 weeks in each half of a cage separated by an opaque partition, groups of three male mice (four cages per compound and per dose) receive the compounds to be tested by the intraperitioneal route in suspension in an aqueous solution of gum arabic, the control animals (six cages) receiving only the aqueous solution of gum arabic. Half an hour later, the two groups of the same cage are brought together by removing the opaque partition and the number of fights which occur in 10 minutes is noted. The results shown in Table II show that, even at the dose of 256 mg/kg which excites the mice, the halogeno derivatives of formula I clearly inhibit the inter-group aggressiveness by reducing the number of fights with respect to the controls, which the psychotonic agent A1 does not do.

TABLE II

| Compound | Code No. | Dose mg/kg | Variation of inter-group aggressiveness |
|---|---|---|---|
| Example 1 | CRL 40941 | 256 (a) | −20% |
| Example 1 | CRL 40941 | 128 | −61% |
| Example 1 | CRL 40941 | 64 | −58% |
| Example 2 | CRL 40933A | 256 (a) | −22% |
| Example 2 | CRL 40933A | 128 | −57% |
| Example 2 | CRL 40933A | 64 | −51% |
| A1 | CRL 40028 | 256 (a) | +36% |
| A1 | CRL 40028 | 128 | −3% |
| A1 | CRL 40028 | 64 | +2% |

Note
(a) dose provoking excitation in the mouse

According to the invention, a therapeutical composition is recommended which is characterized in that it contains, in association with a physiologically acceptable excipient, at least one compound of formula I as active ingredient. The active ingredient will, of course, be used at a pharmaceutically effective dose.

The halogeno derivatives according to the invention may be prepared according to a method known per se by application of conventional reaction mechanisms. The recommended method, successively comprises (a) reacting an alkyl halogenobenzhydrylthioacetate of the formula:

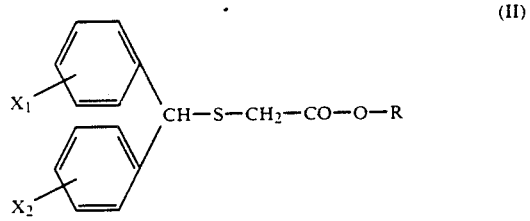

(II)

(wherein $X_1$ and $X_2$ are defined as indicated hereinabove and R represents a $C_1$-$C_2$-alkyl group) with hydroxylamine in stoichiometric quantities in the presence of Na, NaOH or KOH and in an alcohol ROH (wherein R is defined as indicated hereinabove), to obtain the corresponding halogeno-benzhydrylthioacetohydroxamic acid of formula:

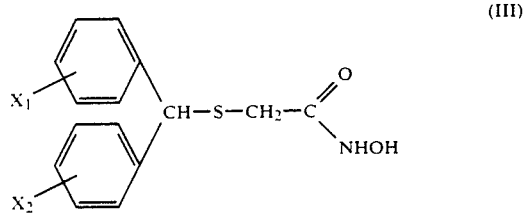

(III)

(b) subjecting the acid (III) thus obtained to oxidation by means of $H_2O_2$ at 110–130 volumes (i.e. an aqueous composition containing from about 32 to about 40% by weight of hydrogen peroxide), in acetic acid and at a temperature lower than 45° C.

Other advantages and features of the invention will be more readily understood on reading the following examples of preparation which are in no way limiting but which are given by way of illustration.

PREPARATION I

Obtaining of 4,4'-difluorobenzhydrylsulfinylacetohydroxamic acid
(Example 1; Code No.: CRL 40941)

(a) 4,4'-difluorobenzhydrylthioacetohydroxamic acid 14.7 g (0.05 mol) of difluorobenzhydrylthioacetic acid (m.p. 117°–118° C.) in solution in 50 ml of dichloroethane are treated with 6 ml of methanol and 0.5 ml of concentrated sulfuric acid. After 6 hours at reflux, the mixture is washed with water, with dilute bicarbonate, dried and evaporated in vacuo.

The oily residue, which essentially comprises methyl 4,4-difluorobenzhydrylthioacetate, is treated overnight at 20° C. with a solution obtained with 2.3 g (0.1 Atg) of sodium, 3.5 g (0.05 mol) of hydroxylamine hydrochloride and 160 ml of anhydrous methanol.

The mixture is evaporated to dryness in vacuo, taken up in 200 ml of water, filtered over charcoal, acidified with 3N HCl, extracted with ether, washed in water, dried, evaporated and the residue of evaporation is crystallized from petroleum ether. The expected hydroxamic acid is obtained (m.p.=75°–76° C.) with a yield of 85%.

(b) CRL 40941

14.2 g (0.046 mol) of 4,4-difluorobenzhydrylthioacetohydroxamic acid in solution in 50 ml of acetic acid is oxidized with 4.6 ml of hydrogen peroxide at 110 volumes. The acetic acid is evaporated in vacuo, taken up in water, drained and washed with water. By crystallization in the methanol-water (50:50) v/v mixture, CRL 40941 is obtained with an overall yield of 60% (m.p.=90°–91° C.).

PREPARATION II

Obtaining of 4-chlorobenzhydrylsulfinylacetohydroxamic acid
(Example 2; Code No.: CRL 40933A)

According to the method described in Preparation I, by replacing the 4,4'-difluorobenzhydrylthioacetic acid by 4-chlorobenzhydrylthioacetic acid (m.p. 101°–102° C.), methyl 4-chlorobenzhydrylthioacetate is obtained (which is not isolated), 4-chlorobenzhydrylthioacetohydroxamic acid, then, by oxidation by means of $H_2O_2$, CRL 40933A.

The results of the tests carried out with CRL 40941 (product of Example 1) concerning its neuropsychopharmacological properties are summarized hereinbelow. In these tests, CRL 40941 was administered by the intraperitoneal route, in suspension in an aqueous solution of gum arabic, in a volume of 20 ml/kg in the male mouse, and in a volume of 5 ml/kg in the male rat.

I-TOXICITY

The LD-0 (maximum non-lethal dose) of CRL 40941 by the IP route in the male mouse is higher than 512 mg/kg.

One third of the mice receiving 1024 mg/kg IP of CRL 40941 present abdominal cramps, depressed respiration, and sedation 45 mins. after administration, then die 24 hours after administration.

II-OVERALL BEHAVIOUR AND REACTIVITIES

Batches of 3 animals are observed before, then 15 mins., 30 mins., 1 hour, 2 hrs., 3 hrs. and 24 hrs. after administration. The following is observed:

(1) in the mouse
at the dose of 256 mg/kg:
fleeting sedation (lasting 0.25 hrs.) then excitation for 3 hrs.
hypothermia ($-1.9°$ C.) for 3 hrs., and
hypermotility,
at the dose of 64 mg/kg:
fleeting sedation lasting less than 0.25 hrs.
at the dose of 16 mg/kg:
fleeting sedation (duration less than 0.25 hrs.)
(2) in the rat
at the dose of 128 mg/kg:
excitation during the first hour following administration,
increase in the reactivity to touch for 1 to 3 hrs.
depressed respiration for 0.5 hrs.,
mydriasis for more than 3 hrs.,
at the dose of 32 mg/kg:
sedation of 0.5 hrs. and
depressed respiration for 0.5 hrs.

III-TESTS ON THE CNS

A-INTERACTION WITH APOMORPHINE (1) In the mouse

Batches of 6 mice receive CRL 40941 half an hour before the sub-cutaneous injection of apomorphine, at the dose of 1 or 16 mg/kg.

It is observed that CRL 40941 leaves unchanged the hypothermia, the posture of verticalization and the stereotypies induced by apomorphine in the mouse.

(2) In the rat

CRL 40941 is administered to batches of 6 rats half an hour before the sub-cutaneous injection of 0.5 mg/kg of apomorphine. It is observed that, particularly at the dose of 128 mg/kg, CRL 40941 prolongs the duration of the stereotypies produced by apomorphine in the rat, whilst CRL 40028, already known, at the dose of 256 mg/kg, does not modify the stereotyped behaviour induced by apomorphine in the rat.

B-INTERACTION WITH AMPHETAMINE

The amphetamine (2 mg/kg) is injected by the intraperitoneal route to batches of 6 rats half an hour after administration of CRL 40941. It is observed that, particularly at the dose of 128 mg/kg, CRL 40941 potentializes the amphetaminic stereotypies in duration, whilst CRL 40028 at the dose of 256 mg/kg does not modify the stereotype behaviour due to amphetamine.

C-INTERACTION WITH RESERPINE

Four hours after the intraperitoneal injection of 2.5 mg/kg of reserpine, batches of 6 mice receive CRL 40941. It is noted that, at a high dose (128 mg/kg), CRL 40941 very moderately reduces the intensity of the ptosis induced by reserpine but does not modify the hypothermia.

D-INTERACTION WITH OXOTREMORINE

CRL 40941 is administered to batches of 6 mice half an hour before the intraperitoneal injection of 0.5 mg/kg of oxotremorine.

1-Action on the temperature

At all the doses used, CRL 40941 opposes very partially the hypothermia-inducing action of oxotremorine, but this very limited antagonism does not increase with the dose.

2-Action on the tremors

CRL 40941 does not substantially modify the tremors due to oxotremorine.

3-Action on the peripheral cholinergic symptoms

CRL 40941 leaves virtually unchanged the signs of peripheral cholinergic stimulation produced by oxotremorine.

E-ACTION ON THE FOUR-PLATE, TRACTION AND ELECTRIC SHOCK TEST

The test is carried out on batches of 10 mice, half an hour after the administration of CRL 40941.

It is observed that CRL 40941 does not increase the number of passes which entail pain. It does not provoke any major motorial deficit and, unlike CRL 40028 mentioned above, it does not modify the convulsivant and lethal effects of the electric shock.

F-ACTION ON THE SPONTANEOUS MOTILITY

Half an hour after having received CRL 40941, the mice (6 per batch, 12 controls) are placed in an activity-meter where their motility is recorded for 30 mins.

At the doses of 64 and 256 mg/kg, it is observed that CRL 40941 stimulates the spontaneous motorial activity of the mouse.

G-ACTION WITH RESPECT TO SOME BEHAVIOURS DISTURBED BY VARIOUS AGENTS (1) Motility reduced by habituation to the enclosure After 18 hrs. sojourn in the activity-meters, the mice (6 per dose, 12 controls) receive CRL 40941. They are immediately returned to their respective enclosures and, half an hour later, their motility is recorded for 30 mins.

At the doses of 64 and 256 mg/kg, CRL 40941 provokes a very clear resumption of the activity in the mouse habituated to its encosure. At a lower dose (4 and 16 mg/kg), this effect is less distinct.

(2) Motility reduced by hypoxic aggression

Half an hour after having received CRL 40941, the mice (10 per dose, 20 controls) are subjected to an acute hypobar anoxia [depression of 600 mm Hg (i.e. about $8 \times 10^4$ Pa) in 90 s, then expansion of 45 s], then they are placed in an activity meter where their mobility is recorded for 10 mins.

At the doses of 16, 64 and, especially, 256 mg/kg, it is observed that CRL 40941 brings about an improvement in the motorial recovery in the mouse whose motility had been depressed further to a brief spell in an enclosure at reduced pressure.

(3) Asphyxic anoxia

Batches of 10 mice receive CRL 40941 half an hour before the intraperitoneal administration of 32 mg/kg of gallamine triiodoethylate.

At a high dose (256 mg/kg), CRL 40941 shortens the time of appearance of convulsions and death consecutive to an asphyxic anoxia provoked by gallamine triiodoethylate which is a reference curariform.

H-INTERACTION WITH BARBITAL

Half an hour after administration of CRL 40941, batches of 10 mice receive an intraperitoneal injection of barbital (220 mg/kg).

At the doses of 64 and 128 mg/kg, CRL 40941 clearly reduces the duration of sleep induced by the barbiturate.

I-CONCLUSION

CRL 40941 has neuropsychopharmacological properties similar to those of CRL 40028 which is a known psychotonic agent. It differs from the latter by its anitagressive properties and its action with respect to electric shock.

It has also been observed that CRL 40941 presents another advantage over CRL 40028 regarding assimilation by the oral route; in fact, CRL 40941, as psychotonic agent, is clearly more effective by the oral route, in the rat and in man, than CRL 40028.

From the clinical point of view, CRL 40941 acts at doses which are half those of CRL 40028. Excellent results were obtained in man when it was administered per os, at the rate of 2 to 3 capsules or tablets (each containing 50 mg of active ingredient) per day, particularly for 2 to 8 weeks in the treatment of hypersommia and psychastenia.

What is claimed is:

1. A benzhydrylsulfinylacetohydroxamic acid derivative of the formula

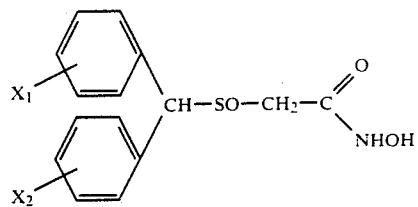

wherein, $X_1$ and $X_2$ are F located in the para (4) position.

2. A therapeutic compound comprising a pharmaceutically effective amount of the compound according to claim 1 in association with a physiologically acceptable excipient.

* * * * *

UNITED STATES PATENT AND TRADEMARK OFFICE
CERTIFICATE OF CORRECTION

PATENT NO. : 4,489,095
DATED : December 18, 1984
INVENTOR(S) : Louis Lafon

It is certified that error appears in the above-identified patent and that said Letters Patent is hereby corrected as shown below:

Col. 1, line 27, "benzhydrylsufinylpro-" should read -- benzhydrylsulfinylpro- --;

Col. 1, line 36, "3686" should read -- '686 --;

Col. 2, line 15, "principle" should read -- principal --;

Col. 5, line 15, "reacitivity" should read -- reactivity --;

Col. 6, line 31, "encosure" should read -- enclosure --;

Col. 6, line 63, "anit-" should read -- anti- --; and

Col. 7, line 11, "hypersommia" should read -- hypersomnia --.

Signed and Sealed this

Twenty-seventh Day of August 1985

[SEAL]

Attest:

DONALD J. QUIGG

*Attesting Officer*   *Acting Commissioner of Patents and Trademarks*